(12) United States Patent
Roller

(10) Patent No.: US 12,144,783 B1
(45) Date of Patent: Nov. 19, 2024

(54) DOSE TRACKING DEVICE

(71) Applicant: ASD Specialty Healthcare, LLC, Conshohocken, PA (US)

(72) Inventor: Dustin James Roller, McKinney, TX (US)

(73) Assignee: ASD Specialty Healthcare, LLC, Conshohocken, PA (US)

( * ) Notice: Subject to any disclaimer, the term of this patent is extended or adjusted under 35 U.S.C. 154(b) by 0 days.

(21) Appl. No.: 18/420,298

(22) Filed: Jan. 23, 2024

Related U.S. Application Data

(60) Provisional application No. 63/514,459, filed on Jul. 19, 2023, provisional application No. 63/498,436, filed on Apr. 26, 2023.

(51) Int. Cl.
  *A61J 7/04* (2006.01)
  *G16H 20/13* (2018.01)

(52) U.S. Cl.
  CPC ............ *A61J 7/0427* (2015.05); *G16H 20/13* (2018.01)

(58) Field of Classification Search
  CPC ........ A61J 7/0427; A61J 7/0436; G16H 20/13
  USPC ....... 206/531, 532, 528, 538, 701, 706, 722, 206/724, 726, 728
  See application file for complete search history.

(56) References Cited

U.S. PATENT DOCUMENTS

| | | | |
|---|---|---|---|
| 6,328,033 B1 * | 12/2001 | Avrahami | A61M 15/001 128/203.19 |
| 10,278,287 B2 | 4/2019 | Wilson et al. | |
| 11,021,306 B2 | 6/2021 | McNannay et al. | |
| 12,023,170 B2 * | 7/2024 | Rogers | G05B 19/042 |
| 2004/0260470 A1 * | 12/2004 | Rast | G06Q 10/0637 705/337 |
| 2016/0158109 A1 | 6/2016 | Nova et al. | |
| 2020/0256815 A1 | 8/2020 | Mehregany | |
| 2022/0249327 A1 | 8/2022 | Joyce et al. | |
| 2023/0204652 A1 * | 6/2023 | Lee | G01R 19/16576 324/763.01 |

OTHER PUBLICATIONS

Conductive Carbon Paste CP-1000, Eteb Guangdong Nanhai ETEB Technology Co., Ltd., Ver. 1.1, Update: Sep. 28, 2020, 2 pages.
ProHere® E 00016, Technical Data Sheet, Michelman®, Inc., revised Nov. 2, 2016, 2 pages.

(Continued)

*Primary Examiner* — Jacob K Ackun
(74) *Attorney, Agent, or Firm* — Klarquist Sparkman, LLP

(57) ABSTRACT

Aspects of a dose tracking device configured for use with commercial packages or "blister cards" of medicaments are disclosed. Disclosed tracking devices track the removal of medicament doses from the "blister cards" with which they are associated. Certain disclosed aspects concern an electronic tracking module comprising plural voltage sensors electrically coupled to a circuit trace that is applied to a medicament blister card obtained commercially or provided by a health care provider. The circuit trace comprises plural circuits that align with medicament blisters containing a medicament dose. When a dose is dispensed from a blister, a corresponding circuit of the circuit trace is broken, indicating that the dose has been dispensed. Patient dosing information can be conveyed to a remote server for monitoring and data storage.

22 Claims, 7 Drawing Sheets

(56) References Cited

OTHER PUBLICATIONS

Silver Paste Material Safety Data Sheet, undated, 8 pages.
International Search Report and Written Opinion, dated Apr. 4, 2024, issued in corresponding International Application No. PCT/US2024/012530, 12 pages.

* cited by examiner

DOSE TRACKING DEVICE

CROSS-REFERENCE TO RELATED APPLICATIONS

This application claims the benefit of the earlier filing dates of U.S. Provisional Application No. 63/514,459, filed Jul. 19, 2023, and U.S. Provisional Application No. 63/498,436, filed Apr. 26, 2023, each of which is incorporated by reference in its entirety herein.

FIELD

The present disclosure concerns a dose tracking device that can be used in combination with a commercial medicament blister card to register when a dose is dispensed from the card.

BACKGROUND

Pharmacists, care providers and insurers have an interest in ensuring that patients adhere properly to a medication regimen. This is particularly true for very expensive medications and/or for treatments where non-adherence to a dosing protocol can have substantial deleterious effects. Certain medications, such as Hepatitis C medications for example, must be taken at a particular dose at a particular time. Treatment efficacy depends on patient compliance with the dosing protocol. Non-compliance with a dosing protocol can have substantially deleterious effects for individuals, including exacerbating a patient's condition, as opposed to ameliorating or alleviating symptoms associated with a particular malady.

Clinical trials provide another example where patient compliance with the clinical trial dosing protocol is absolutely necessary to obtain reliable dosing and efficacy data. Patient failure to comply with a clinical trial dosing regimen can result in substantial loss of data and increases clinical trial costs.

Prior known devices typically require a user to do something, other than taking a required dose, to note that the dose was taken, and potentially when the dose was taken. For example, certain smart phone applications are available that allow a user to log that a particular dose was taken.

SUMMARY

Disclosed herein are aspects of a dose tracking device configured for use with commercial packages or "blister cards" of lozenges, therapeutics, pills, or other medicament dosages, collectively referred to herein as medicaments. Disclosed tracking devices can track the removal of medicament doses from the "blister cards" with which they are associated. One feature of certain disclosed aspects is that they eliminate the requirement for a user to input or otherwise record an event.

Certain disclosed aspects concern an electronic tracking module comprising plural voltage sensors electrically coupled to a circuit trace that is applied to a medicament blister card obtained commercially or provided by a health care provider. While blister cards of various dimensions and number of medicaments may be available, blister cards are most typically 4 pills×8-pills blister cards. The circuit trace comprises plural circuits that align with medicament blisters containing a medicament dose. When a dose is dispensed from a blister, a corresponding circuit of the circuit trace is broken. This reduces total circuit voltage and increases total circuit resistance, thereby indicating that the dose has been dispensed. A person of ordinary skill in the art will appreciate that circuit voltage and resistance are correlated according to Ohm's law by the formula $E=I \times R$, or voltage=current×resistance. For certain aspects, the circuit trace comprises plural conductive metal pads, such as silver pads, configured to provide electrical connection to the device. The circuit trace also includes plural semiconductor circuits. These semiconductor circuits may be applied using any suitable technique, such as using a semi-conductive ink, typically a carbon-based ink, one example of which is a graphite ink, that align with blisters on the medicament blister card.

The device typically comprises plural metal clamps that firmly associate the device with the blister card. For certain aspects, the clamps deflect upon insertion of the blister card and return to an undeflected position to secure the device to the blister card. The clamps may be, for example, J clamps that engage a clamp protrusion to lock the clamp and blister card in place. The device may include additional features that facilitate firmly associating a blister card with the device. For example, the device may comprise a blister card receiving slot that is sized to pressure fit the blister card with the device. This pressure fit can be facilitated by providing shoulders that engage an inserted blister card to produce a slight pucker in the inserted blister card so that the card engages the device under tension to secure the card to the device. The device may also comprise an external shelf (certain disclosed aspects include a small shelf, such as a 1 millimeter to 5-millimeter protruding shelf) upon which at least a portion of the blister card rests to further prevent movement of the blister card relative to the device.

Certain disclosed aspects further comprise alignment protrusions to facilitate aligning the device with the blister pack and circuit trace. These protrusions may be configured to align with, for example, a metallic pad of the circuit trace.

For certain disclosed aspects, total circuit voltage decreases and total circuit resistance increases predictably as a medicament is dispensed from each blister. As a result, a number of medicament doses remaining in blisters on the blister card can be determined by correlating the circuit voltage or resistance to the number of broken or unbroken blisters.

The dose tracking device typically comprises an electronic control board for controlling device functions. The control board includes plural electrical connectors for electrical connection with the circuit trace. The plural electrical connectors may be any suitable connector, such as spring-biased connectors, pin connectors, leaf spring connectors, or any combination thereof. The device may be a cellular connected device, as Bluetooth device, a WiFi device, or any combination thereof. One disclosed aspect was configured for use as a cellular connected device, and therefor includes a suitable module, such as an NB-IoT module or a combination NB-IoT and LTE CAT-M1 module. NB-IoT networks are broadly available in China and some EU markets, whereas LTE CAT-M1 networks are typically used in other major markets, such as Canada, Japan, and the United States. The board also may include a microcontroller, a rechargeable power source, a USB port for charging, and/or an LED to indicate on:off and/or charging status.

The device may be used in association with a remote server for receiving data from the device. The device also may comprise re-try logic whereby the device attempts a connection with the blister card and/or transmits data to the remote server periodically. The device may, for example, attempt to connect every 15 minutes. The device is configured to connect at least once every 24 hours.

Disclosed aspects of the device may be made using any suitable method, such as injection molding or 3-D printing from a polymeric material. The device may comprise a unitary device, a clam shell device, or a device comprising separable components.

A particular aspect of a disclosed dose tracking device configured for use in association with a commercial medicament blister card comprises a receiving slot sized to provide a pressure fit for a commercially available medicament blister card inserted into the device, the device further comprising shoulders that engage an inserted blister card to produce a slight pucker in the inserted blister card so that the card engages the device under tension and a shelf upon which at least a portion of the blister card is in contact to further prevent movement of the blister card relative to the device. The device comprises plural voltage sensors configured to electrical couple to a circuit trace applied to the medicament blister when the card and circuit trace are inserted into the device. The circuit trace comprise plural conductive metal pads configured to provide electrical connection to the device, and plural semiconductor circuit traces that align with blisters on the medicament blister card. Alignment protrusions facilitate aligning the device with the blister pack and the circuit trace, and plural metal clamps hold the blister card in position relative to the device. When a dose is expelled from a blister, a corresponding circuit of the circuit trace is broken, thereby reducing total circuit voltage and increasing total circuit resistance, indicating that the dose has been dispensed. A control board controls device functions, and comprises a microcontroller, a rechargeable power source, a USB port, and/or an LED to indicate on:off and/or charging status.

Aspects of an adhesive circuit trace configured for application to a blister card and electrical connection with a dose tracking device also are disclosed. The adhesive circuit trace may comprise a front side comprising plural metal conductive pads for electrical association with a dose tracking device, and further comprising plural circuits electrically associated with the metal conductive pads. The plural circuits are configured to align with blisters on a blister card and to measure voltage or resistance across an individual circuit aligned with each medicament blister. The circuit trace comprises a back side comprising an adhesive and an adhesive cover sheet that can be removed to adhere the circuit trace to a medicament blister card. In one aspect, the trace adhesive was an ethylene acrylic acid copolymer, such as ProHere E 00016 adhesive.

Aspects of a method comprising using a dose tracking device, a combination comprising the dose tracking device, and/or a circuit trace, also are disclosed. The method may comprise providing a dose tracking device to a user together with instructions concerning inserting the medicament blister card into the device to appropriately align the trace with electrical sensors on the device. The user inserts the medicament blister card into the device, and the device activates upon insertion of the blister card. The device transmits to a remote server that it has been activated and attempts an initial measurement. The controller includes re-try logic. If an initial connection and/or blister measurement is not successful, the device automatically retries to secure such connection and make an initial measurement. The re-try logic can be configured to re-try at particular time intervals, such as every 15 minutes, and the device is programmed to activate at least once every 24 hours to perform a dosage inventory on a blister card associated with the device.

Certain medication protocols require a user to dispense one medicament from the blister card daily. Alternatively, the medication protocol may require a user to dispense multiple doses daily at different administration times. A user dispenses medicament from the medicament blister card as appropriate. Subsequently, the device is activated, and obtains a voltage/resistance measurement. Dispensing a medicament or medicaments from a blister breaks the circuit associated with the particular blisters broken. The voltage of the remaining circuit decreases and the resistance of the remaining circuit increases in a known manner when a blister circuit breaks, and these changes can be correlated to an inventory of medicaments dispensed and/or that are remaining in blisters on the medicament card.

The foregoing and other objects, features, and advantages of the disclosure will become more apparent from the following detailed description, which proceeds with reference to the accompanying figures.

DETAILED DESCRIPTION

I. Abbreviations and Terms

Figure 1:
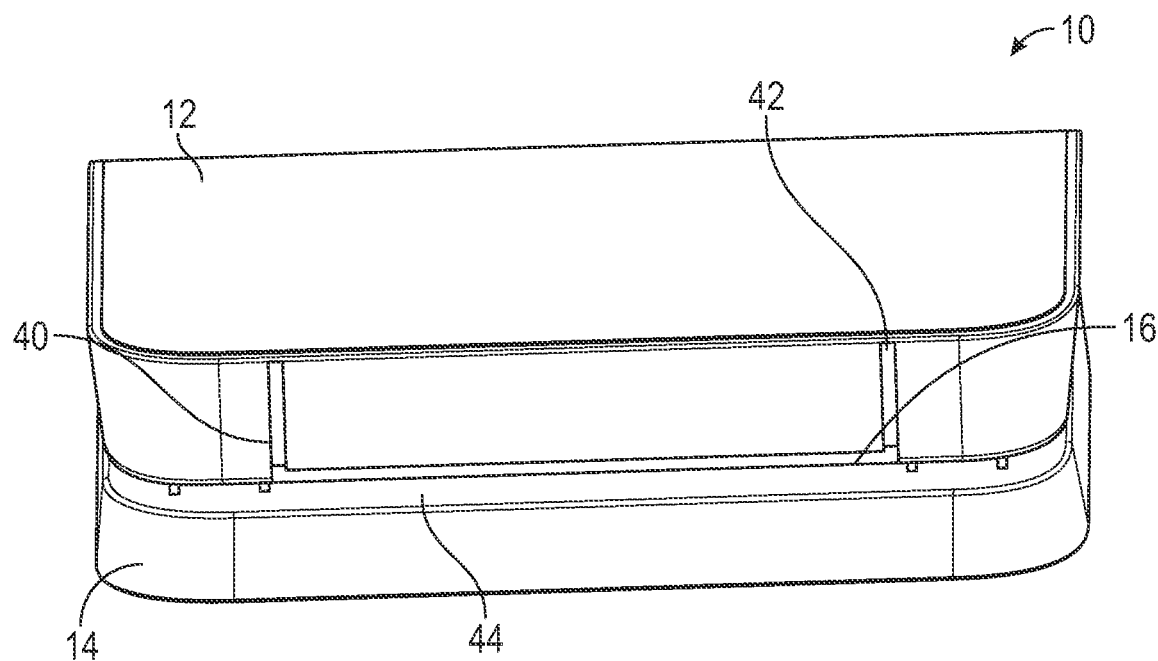
FIG. 1 is an end perspective view of a dose tracking device according to the present disclosure.

The following explanations of terms and abbreviations are provided to better describe the present disclosure and to assist those of ordinary skill in the art to fully comprehend and to facilitate practicing aspects of the present disclosure.

The singular forms "a" or "an" or "the" include plural references unless the context clearly dictates otherwise.

The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used to practice or test the present disclosure, suitable methods and materials are described below. The materials, methods, and examples are illustrative only and are not intended to be limiting. Other features of the disclosure will be apparent from the detailed description and the claims.

The disclosure of numerical ranges should be understood as referring to each discrete point within the range, inclusive of endpoints, unless otherwise noted.

Unless otherwise indicated, all numbers expressing quantities, percentages, temperatures, times, and so forth, as used in the specification or claims are to be understood as being modified by the term "about." Accordingly, unless otherwise implicitly or explicitly indicated, or unless the context is properly understood by a person of ordinary skill in the art to have a more definitive construction, the numerical parameters set forth are approximations that may depend on the desired properties sought and/or limits of detection under standard test conditions/methods as known to those of ordinary skill in the art. When directly and explicitly distinguishing aspects from discussed prior art, the aspect numbers are not approximates unless the word "about" is recited.

Although there are alternatives for various components, parameters, operating conditions, etc. set forth herein, that does not mean that those alternatives are necessarily equivalent and/or perform equally well. Nor does it mean that the alternatives are listed in a preferred order unless stated otherwise.

Blister card: Blister packaging is a type of packaging produced by heating a sheet of plastic and molding it into shape to form a bubble or pocket, referred to as the 'blister,' that completely covers the product. A traditional blister pack is known as a face seal blister and has a cardboard back. Blister cards can be used to house medicaments to provide controlled single or multiple unit doses for patients. There is a direct correlation between use of blister packs and improved patient compliance/adherence to dosing regimens. Blister packs provide a visual dose history, and are generally easier to use, particularly for patients taking multiple pills per dose and those who have difficulty remembering proper dosage protocols. While medicament blister card sizes and shapes may vary, blister cards for medicaments are often 4 inch (10 cm) by 8 inch (20 cm) rectangles.

Patient or Subject: Refers to mammals and other animals, particularly humans. Thus disclosed methods are applicable to both human therapy and veterinary applications. An animal (human or non-human) that may be administered a dose from a pack, such as a blister pack, and including both human and veterinary subjects.

Treating or treatment: Either term includes (1) preventing a disease, e.g., causing the clinical symptoms of the disease not to develop in a subject that may be exposed to or predisposed to the disease but does not yet experience or display symptoms of the disease, (2) inhibiting the disease, e.g., arresting the development of the disease or its clinical symptoms, or (3) relieving the disease, e.g., causing regression of the disease or its clinical symptoms.

Unit Dose: A drug or pharmaceutical composition in a single or metered dose form, such as a table, capsule, powder or solution to be administered as a single dose, or multiple preselected doses.

II. Dose Tracking Device

1. Device

Figure 2:
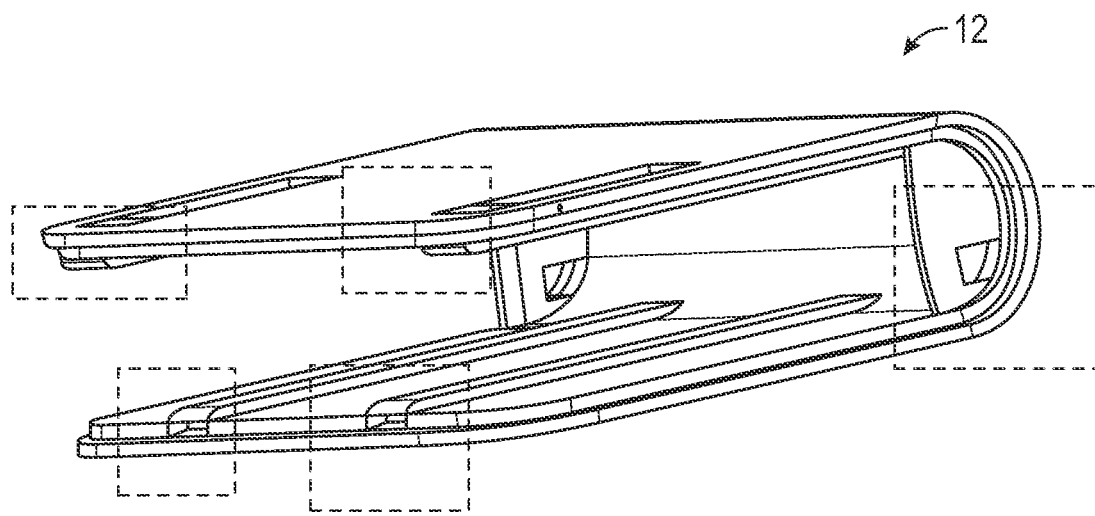
FIG. 2 is a perspective view of an outer clam shell portion of a dose tracking device according to the present disclosure.

FIG. 1 provides an external perspective view of a dose tracking device 10 according to the present disclosure. FIG. 2 is an enlarged end view of the dose tracking device illustrated in FIG. 1. FIG. 1 illustrates a design comprising a portion 12 shaped to engage and fit about a portion 14. Top portion 12 is shown disassembled from portion 14 in FIG. 2. The illustrated device 10 is sized to accommodate most commercial blister cards, such as 4-medicament×8-medicament blister cards. As used herein, the terms "medicament" and "medication" are interchangeable.

Figure 6:
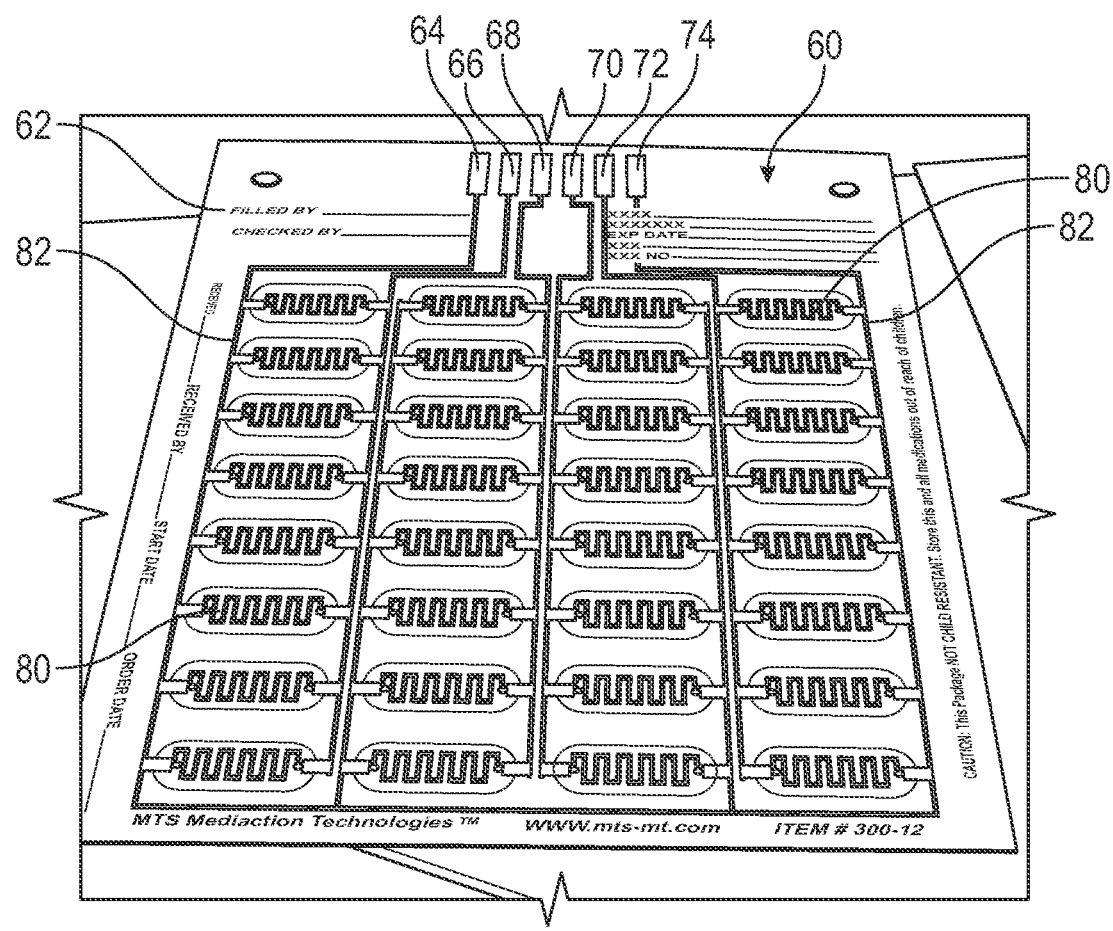
FIG. 6 is a perspective view of one aspect of an adhesive label comprising a circuit trace having plural circuits for use in combination with a dose tracking device according to the present disclosure.

Top portion 12 and bottom portion 14 mated together define a receiving slot 16 into which a blister card is inserted to provide a pressure fit. Device 10 also may include alignment protrusions 18, 20 (FIG. 3), to facilitate aligning the device appropriately with an inserted blister card. Alignment protrusions 18, 20 facilitate alignment with adhesive circuit traces that are used in combination with device 10 and are applied to blister cards, including by an end user. FIG. 6 shows an aspect of an adhesive circuit trace 60, discussed in more detail below, comprising a front side 62 with plural conductive metal (such as silver) pads 64, 66, 68, 70, 72 and 74. Alignment protrusions 18, 20 align with these pads 64-72. For example, protrusion 18 may be aligned with a center portion of conductive metal trace 64 and protrusion 20 may be aligned with a center portion of trace number 74. Device 10 also includes plural pairs of connecting apertures 46 for receiving connecting pins for spring-biased electrical connectors, as discussed in more detail with reference to FIG. 8.

A person of ordinary skill in the art will appreciate that the dose tracking device does not have to be configured as a mated component design. The device might have a unitary design. As yet additional alternative designs, the device 10 may be configured as a clam shell device that closes about a blister pack, or as two separate components with one component comprising coupling components that penetrate through a blister pack and connect the first component to the second component.

Device 10 can be made from any suitable materials. For certain disclosed aspects, the device 10 was 3-D printed using suitable polymeric materials. Certain commercial aspects likely will be injection molded using a suitable polymeric material, such as ABS+PC plastic with a V-0 fire rating (UL 94 V-0).

Figure 4:
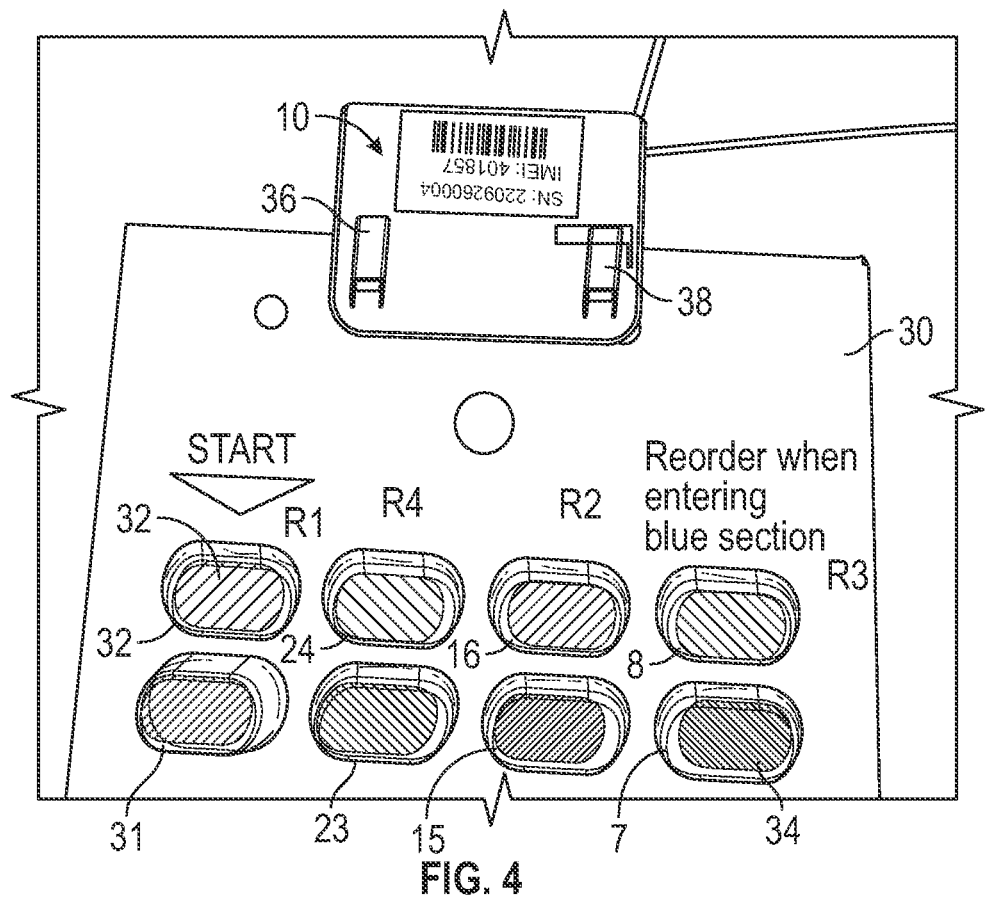
FIG. 4 is a plan view of a dose tracking device according to the present disclosure associated with a commercially available blister pack comprising plural medicaments.

FIG. 4 illustrates a dose tracking device 10 according to the present disclosure associated with a blister card 30 having plural blisters 32 that house individual doses 34. Metal clamps 36, 38 firmly associate the device 10 with the blister card 30 while allowing non-destructive reuse of the device 10. One aspect of device 10 includes hinged clamps 36, 38 (See FIG. 5) that deflect upon insertion of a blister card 30 and are spring biased to secure the device 10 to the blister card 30.

Figure 5:
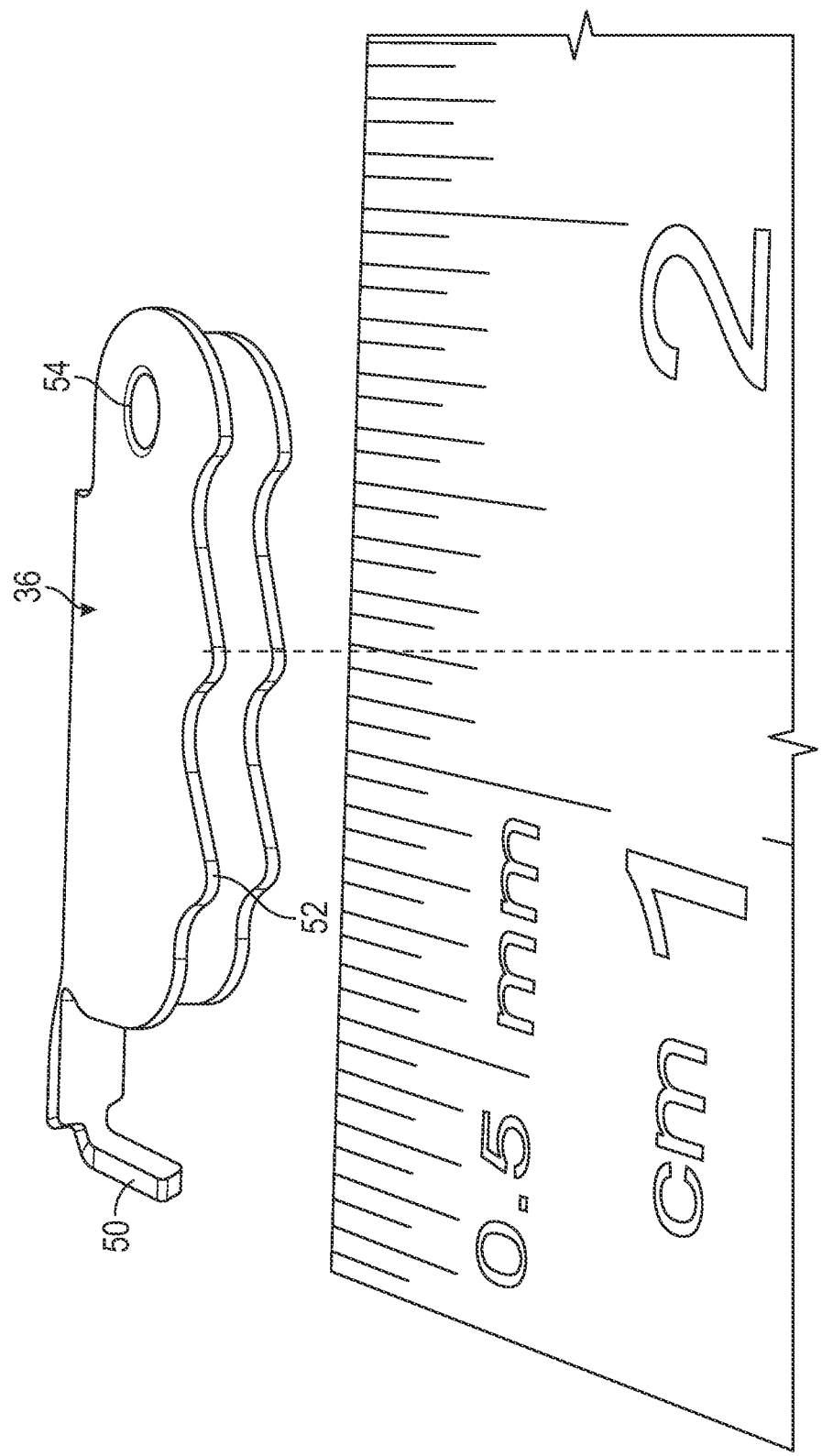
FIG. 5 is a perspective view of one aspect of a clamp for firmly associating a blister pack with a dose tracking device according to the present disclosure adjacent a ruler to provide an estimate of the clamp size.

With reference to FIG. 5, metal (e.g. steel) clamp 36 includes a first end 50 and plural teeth 52 that engage blister card 30 by rotation about 54. The illustrated aspect includes an L-shaped end 50. A person of ordinary skill in the art will realize that other shapes, such as a J-shape, are also effective. For certain aspects, a clamp 36 having a J-shape end can be used such that the J curve engages a protuberance (not shown) to further lock the clamp in place. Clamps 36 are rotatably coupled to the device to facilitate insertion and removal of a blister card. Accordingly, clamp 36 includes connecting pin slot 54 into which a connecting pin is inserted and about which clamp 36 can rotate in and out of contact with a blister card 30. To remove the device 10 from the card 30 once all doses have been administered, the user can remove the card by manually deflecting the clamps upwardly and away from the blister card.

Figure 3:
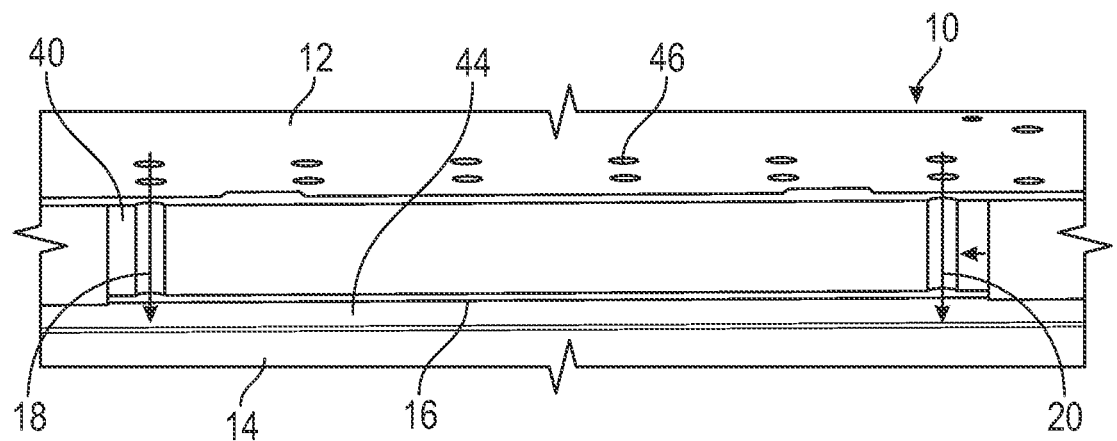
FIG. 3 is an end view of a dose tracking device according to the present disclosure illustrating the use of alignment protrusions to facilitate aligning an inserted blister card with the dose tracking device.

FIGS. 1 and 3 also show that the device 10 can include slight indentations or shoulders 40, 42, and a shelf 44. Shelf 44 in the illustrated aspect is small, about 1 millimeter to about 5 millimeters deep. Shoulders 40, 42 produce a slight pucker in the blister card 30 so that the card engages the device 10 under tension to further secure the card to the device by friction. These features, in combination with clamps 36, 38, help prevent movement of the blister card 30 relative to the device 10.

Dose tracking device 10 has to be electrically connected to a blister card in order to register a user's removal of a dose from a blister. This can be achieved using an adhesive circuit trace, as illustrated by the circuit trace 60 of FIG. 6. As discussed above, circuit trace 60 can be effectively electrically aligned with a dose tracking device 10 using alignment protrusions 18, 20. Circuit trace 60 comprises a printed top portion 62 onto which plural electrical connecting pads 64-74 are deposited/printed. Pads 64, 66, 68, 70, 72 and 74 are made from a conductive metal, such as silver. Circuit trace 60 also includes plural (horizontally oriented in FIG. 6) blister circuits 80 that align with medicament blisters 32 on card 30. Circuit trace 60 also includes plural connector traces 82 (vertically oriented in FIG. 6) that interconnect device 10 with each of the plural blister circuits 80. For certain disclosed aspects, the blister circuits 80 were made from a semiconductor material, such as graphite or other carbon-based semiconductor ink, whereas connector traces 82 were made from a low or no resistance material, such as silver. Certain disclosed aspects produced circuits using conductive carbon paste CP-100, which is particularly designed for printing flexible printed circuits. Connector traces 82 were applied for certain aspects using a silver flake/polyester resin composition, such as can be obtained from Guangdong Nanhai ETEB Technology Co., Ltd., Foshan City, China.

One method for tracking medicaments as they are dispensed from a blister card comprises electrically coupling individual circuits to each of the blisters: the circuit is either intact prior to dispensing, or the circuit is broken subsequent to dispensing. This approach is an on:off arrangement and would require that the circuit trace have 32 separate circuits for a blister card comprising 32 blisters. The aspect illustrated in FIG. 6 reduces the number of circuits from 32 that would be required for operation with individual circuits associated with each blister to 4 circuits, and the device measures electrical resistance across the entire circuit. The 4 circuits are associated with the four vertically aligned plural blisters 32. By using a semiconductor material, the circuit voltage decreases and circuit resistance increases predictably as a medicament is dispensed from each blister 32. This provides several advantages, other than simply reducing the electrical circuitry complexity. For example, after a number of doses have been dispensed, the number of remaining doses can be determined by correlating the circuit voltage or resistance to the number of broken or unbroken blisters 32. An electrical current has 8 paths, correlating to the 8 blister circuits 80 across which current can travel. If a single blister 32 is broken, then the voltage of the circuit associated with that blister is decreased and the resistance of that circuit is increased by approximately 12.5%(100/8 traces); if a second blister is broken on that circuit, then the circuit voltage will decrease and the resistance will increase by about 14%(100/7); etc. Finally, when the last medicament on a particular circuit is broken, then no current will flow, as each of the particular electrical circuit paths are broken.

Figure 7:
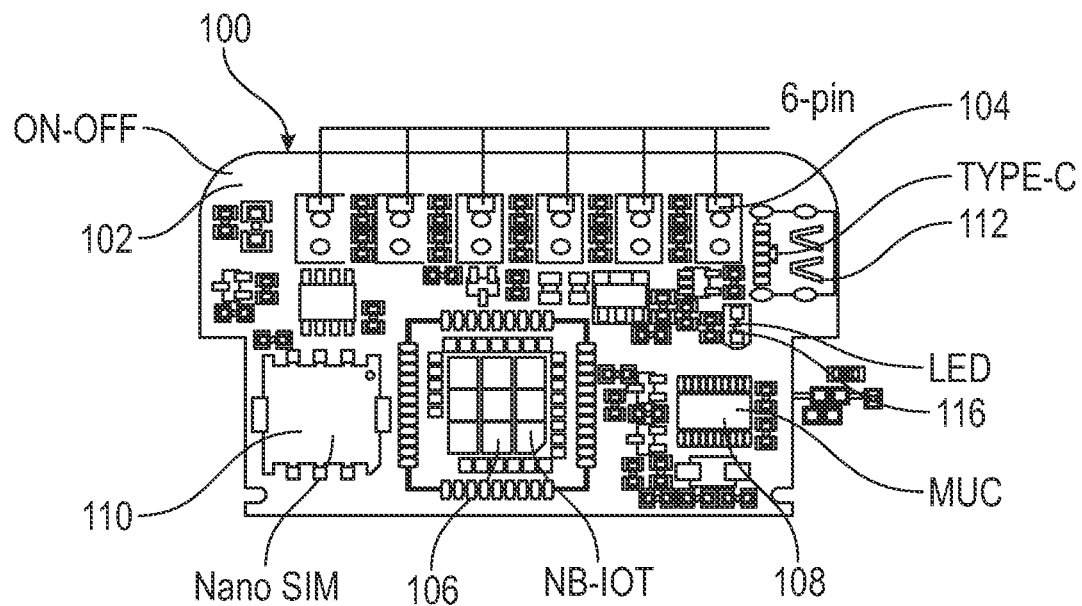
FIG. 7 is a plan view of one aspect of a circuit board for use in connection with disclosed aspects.

FIG. 7 is a plan view of a circuit board 100. Board 100 includes an on-off switch 102 and plural sensor pins 104 for electrical connection to each of the pads 64-74 of circuit trace 60. A person of ordinary skill in the art will appreciate that the number of sensor pins 104 is variable, as are the number of electrical contact pads and circuits printed on circuit trace 60.

Dose tracking device 10 also is configured to convey data. The illustrated aspect of device 10 is particularly designed as a cellular connected device, and therefore includes an NB-IoT module or a combination NB-IoT and LTE CAT-M1 module 106. Device 10 need not be a cellular connected device. Other data conveying techniques also are suitable, including Bluetooth, WiFi, or combinations thereof.

Figure 8:
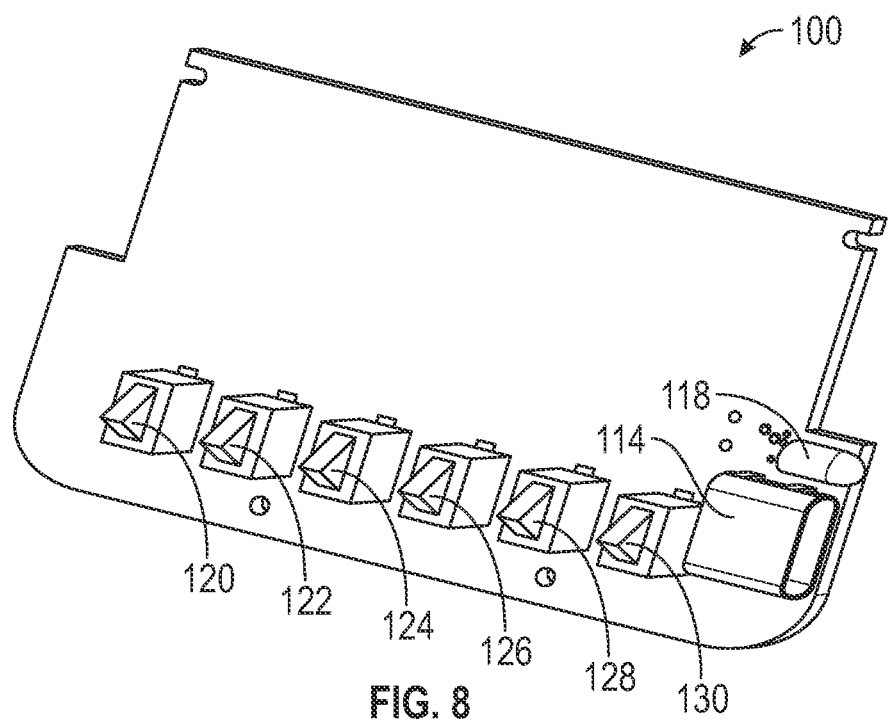
FIG. 8 is a perspective view of a backside of the circuit board of FIG. 7 illustrating a USB charging port, an LED housing and plural spring connectors for electrically connecting the dose tracking device to a medicament blister pack.

Board functions are controlled by microcontroller 108. Data generated by device 10 can be transmitted and/or stored on a memory card, such as a nano-sim card 110. Device 10 also includes a power source, such as a battery (not shown), that can be recharged, with certain aspects comprising a USB type C charger 112. USB i/o port 114 is shown in FIG. 8. Optionally, device 10 can include an LED 116 to indicate certain functions, such as when the device is powered on or off, or is or is not charging. LED housing 118 is shown in FIG. 8.

FIG. 8 provides a perspective view of a back side of control board 100. As discussed above, board 100 includes USB port 114 and LED housing 118. Board 100 also includes plural electrical connectors, such as spring connectors 120, 122, 124, 126, 128 and 130. As a blister card 30 is inserted into device 10, the spring biased connectors 120-130 deflect to receive the card and then are spring-biased back into a secure electrical connection with silver trace pads 64, 66, 68, 70, 72 and 74 on circuit trace 60. These spring-biased connectors 120-130 are robust, and can function appropriately for a reasonable device lifetime. A person of ordinary skill in the art will, however, appreciate that various other methods of electrically connecting device 10 to circuit trace 60 also can be used, such as metal conductive pogo pins or leaf springs that engage the circuit trace once a device 10 is positioned in association with a blister card.

When a dose tracking device 10 is ready for use, a battery pull tab (not shown) is removed. A blister card is inserted into slot 16, and the device activates and attempts an initial measurement. If the device is appropriately connected to the blister card and has a connection to a server, the device transmits to the server that it has been activated. In some aspects, the connection is a cellular, short-range wireless (e.g., Bluetooth® wireless technology, Bluetooth SIG, Inc., Kirkland, WA)), or WiFi connection. If an initial connection is not successful, the controller includes re-try logic and the system automatically retries to obtain such connections and/or make voltage/resistance measurements. This re-try logic can be set for particular time intervals, such as every 15 minutes, and for a particular number of attempts to connect, such as 3 or more times. The device is programmed to activate at least once every 24 hours so that it can, for example, ascertain a dosage inventory on an associated blister card. The device works and transmits pill usage for an extended period of time, such as up to at least 120 days on a single charge. Certain medication protocols require taking multiple doses at multiple different times. By periodically activating, the device 10 can take inventories that account for such medication protocols. Moreover, by taking periodic measurements, certain aspects can be configured to determine an approximate time when a dose was dispensed.

Aspects of a kit comprise a dose tracking device as disclosed herein and instructions for use of the dose tracking device. In some aspects, the kit further includes a medicament blister card.

2. Software/Remote Date Acquisition

Figure 9:
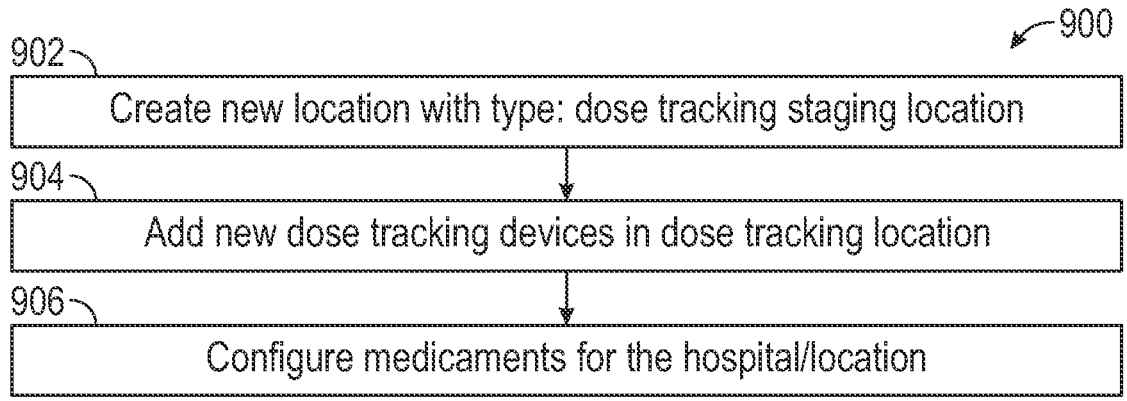
FIG. 9 sets forth certain administrator steps for implementing an exemplary dose tracking workflow using a dose tracking device according to the present disclosure.

Dose tracking devices of the present disclosure are particularly designed to transmit data to a remote server where data can be stored and medicament dispensing can be overseen by an administrator. FIG. 9 sets forth certain steps concerning an exemplary administrator workflow 900. A first action 902 for an administrator is to create a new location and type of location. As used herein, location can refer to a subject to maintain patient confidentiality. A patient need not be unique, but a warning may display if another patient is identified at the same location. The administrator then adds a new dose tracking device at the location at step 904, and configures medicament blister cards for use at the location at step 906.

Figure 10:
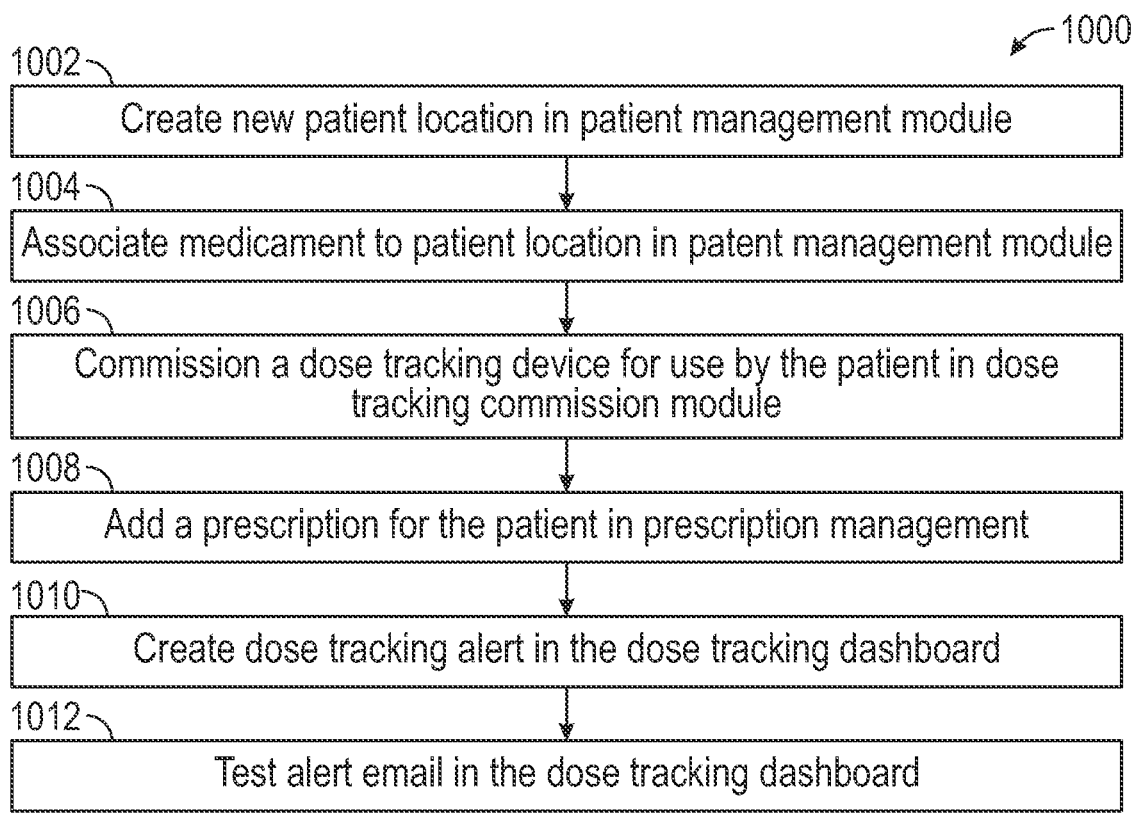
FIG. 10 sets forth certain steps for a controller or supervisor, such as a pharmacist, doctor, or clinical trial administrator, implementing an exemplary dose tracking workflow using a dose tracking device according to the present disclosure.

FIG. 10 sets forth certain steps concerning an exemplary workflow 1000 for an administrating professional, such as a pharmacist, doctor, hospital, or clinical trial administrator. In first step 1002, the professional creates a new patient location in a patient management module. The patient location is then associated with a particular medicament to be administered to be administered to that patient in step 1004. In step 1006, a particular dose tracking device is commissioned for use by a particular patient in a dose tracking commission module. A prescription is added for the patient in prescription management at step 1008. A dose tracking alert is then added to a dose tracking patient dashboard in step 1010, and a test alert email is generated at step 1012 in the patient dose tracking dashboard.

Figure 11:
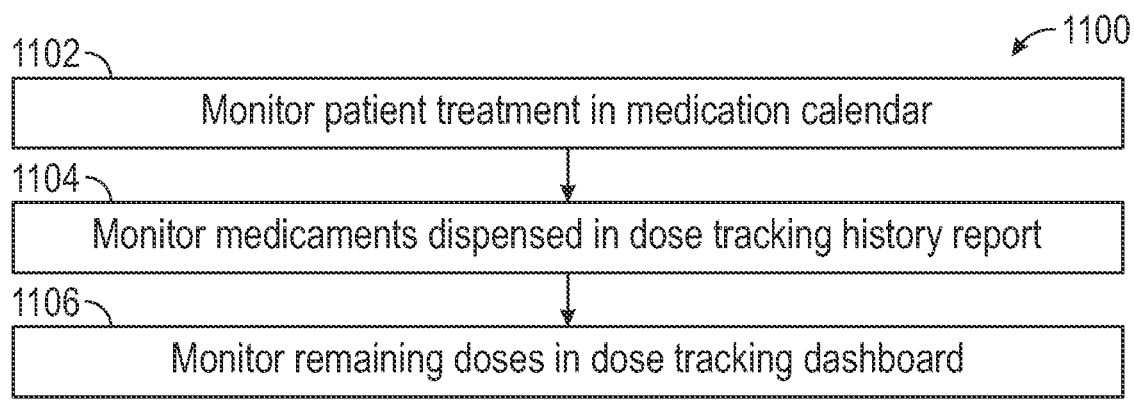
FIG. 11 sets forth certain steps for a technician, such as a pharmacy technician, implementing an exemplary dose tracking workflow using a dose tracking device according to the present disclosure.

Certain steps concerning an exemplary technician workflow 1100, such as a pharmacy technician workflow, are illustrated in FIG. 11. The technician can monitor patient treatment at step 1102 using a medication calendar. As medicaments are dispensed by a patient, the technician can monitor the medicaments dispensed in a dose tracking history report at step 1104. And the technician can monitor dose remaining on a blister card at step 1106.

III. Representative Aspects

Certain representative aspects are exemplified in the following numbered clauses.

1. A dose tracking device configured for use in association with a commercial medicament blister card.
2. The dose tracking device according to clause 1, comprising an electronic tracking module comprising plural voltage sensors electrically coupled to a circuit trace applied to a medication blister card such that circuits of the trace align with medication blisters containing a medicament dose, such that when a dose is dispensed from a blister, a corresponding circuit of the circuit trace is broken, reducing total circuit voltage and increasing total circuit resistance, and thereby indicating that the dose has been dispensed.
3. The device according to clause 2, wherein the circuit trace comprises: plural conductive metal pads configured to provide electrical connection to the device; and plural semiconductor circuit traces that align with blisters on the medication blister card.
4. The device according to clause 3 wherein the conductive metal is silver and the semiconductor is applied as a carbon-based ink.
5. The device according to any one of clauses 1-4, comprising a blister card receiving slot sized to pressure fit the blister card with the device.
6. The device according to any one of clauses 1-5, comprising shoulders that engage an inserted blister card to produce a slight pucker in the inserted blister card so that the card engages the device under tension to further secure the card to the device.
7. The device according to any one of clauses 1-6, further comprising a shelf upon which at least a portion of the blister card is in contact to further prevent movement of the blister card relative to the device.
8. The device according to any one of clauses 1-7, further comprising plural metal clamps to firmly associate the device with the blister card.
9. The device according to clause 8 wherein the clamps deflect upon insertion of the blister card and return to an undeflected position to secure the device to the blister card.
10. The device according to clause 8 or clause 9, comprising J clamps that engage a clamp protrusion to lock the clamp in place.
11. The device according to any one of clauses 1-10, comprising alignment protrusions to facilitate aligning the device with the blister pack and circuit trace.
12. The device according to any one of clauses 1-11 configured for use with a 4×8-inch blister card.
13. The device according to any one of clauses 1-12, wherein circuit voltage and resistance change predictably as medication is dispensed from each blister.
14. The device according to clause 13 wherein a number of doses remaining in blisters on the blister card can be determined by correlating the circuit voltage or resistance to the number of broken or unbroken blisters.
15. The device according to any one of clauses 1-14 comprising a control board for controlling device functions.
16. The device according to clause 15 comprising plural electrical connectors for electrical connection with the circuit trace.
17. The device according to clause 16 wherein the plural electrical connectors are spring-biased connectors, pin connectors, leaf spring connectors, or any combination thereof.
18. The device according to clause 16 wherein the plural electrical connectors are spring-biased connectors.
19. The device according to any one of clauses 1-18, comprising one or more of: a microcontroller; a rechargeable power source; a USB port; and/or an LED to indicate on:off and/or charging status.
20. The device according to any one of clauses 1-19 further in association with remote server for receiving data from the device.
21. The device according to clause 20 comprising re-try logic whereby the device attempts a connection with the blister card and/or transmits data to the remote server periodically.
22. The device according to clause 19 wherein the device attempts to connect every 15 minutes.
23. The device according to clause 19 wherein the device attempts to connect at least once every 24 hours.

24. The device according to any one of clauses 1-23, wherein the device is a cellular connected device, a Bluetooth device, a WiFi device, or any combination thereof.
25. The device according to clause 24, comprising a cellular connected device.
26. The device according to any one of clauses 1-25, wherein such device is injected molded or 3-D printed from a polymeric material.
27. The device according to any one of clauses 1-26, comprising a unitary device, a clam shell device, or a device comprising separable components.
28. A dose tracking device configured for use in association with a commercial medicament blister cards, the device comprising a tracking module that comprises: a receiving slot sized to provide a pressure fit for a commercially available medication blister card inserted into the device, the device further comprising shoulders that engage an inserted blister card to produce a slight pucker in the inserted blister card so that the card engages the device under tension and a shelf upon which at least a portion of the blister card is in contact to further prevent movement of the blister card relative to the device; plural voltage sensors configured to electrical couple to a circuit trace applied to the medication blister when the card and circuit trace are inserted into the device, the circuit trace comprising plural conductive metal pads configured to provide electrical connection to the device, and plural semiconductor circuit traces that align with blisters on the medication blister card, such that when a dose is expelled from a blister, a corresponding circuit of the circuit trace is broken, thereby reducing total circuit voltage and increasing total circuit resistance, indicating that the dose has been dispensed; alignment protrusions to facilitate aligning the device with the blister pack and the circuit trace; plural metal clamps to hold the blister card in position relative to the device; and a control board for controlling device functions comprising a microcontroller, a rechargeable power source, a USB port, and/or an LED to indicate on:off and/or charging status.
29. The device according to clause 28 wherein the conductive metal is silver and the semiconductor is applied as a graphite ink.
30. The device according to clause 28 comprising J-clamps that deflect upon insertion of a blister card and return to an undeflected position to secure the device to the blister card.
31. The device according to any one of clauses 28-30, comprising a unitary device, a clam shell device, or a device comprising separable components.
32. The device according to any one of clauses 28-31 configured for use with a 4×8-inch blister card.
33. The device according to any one of clauses 28-32 further in association with remote server for receiving data from the device.
34. The device according to any one of clauses 28-33 comprising re-try logic whereby the device periodically attempts to connect with the blister card and/or attempts to transmit data to the remote server.
35. The device according to any one of clauses 28-34, wherein the device is a cellular connected device, a Bluetooth device, a WiFi device, or any combination thereof.
36. An adhesive circuit trace configured for electrical connection with a device according to any one of clauses 1-35.
37. The adhesive circuit trace according to clause 36, comprising: a front side comprising plural metal conductive pads for electrical association with a dose tracking device, the front side further comprising plural circuits electrically associated with the metal conductive pads wherein the plural circuits are configured to align with blisters on a blister card and to measure voltage or resistance across an individual circuit aligned with each medicament blister; and a back side comprising an adhesive for securing the circuit trace to a medicament blister card.
38. A combination, comprising: a device according to any one of clauses 1-35; and a medication blister card comprising an adhesive circuit trace according to any one of clauses 36-37 that is applied to the card and electrically associated with the device.
39. A method, comprising using a dose tracking device, a combination comprising the dose tracking device, or a circuit trace according to any one of clauses 1-38.
40. The method according to clause 39, comprising providing a dose tracking device to a user.
41. The method according to clause 40 wherein the user is instructed to insert the medicament blister card into the device to appropriately align the trace with electrical sensors on the device.
42. The method according to clause 40 comprising inserting the medicament blister card into the device.
43. The method according to clause 42 wherein the user dispenses medicament from the medicament blister card.
44. The method according to clause 39, wherein the device is activated upon insertion of a blister card and the device attempts an initial measurement.
45. The method according to clause 44, wherein the device is appropriately connected to the blister card and the device transmits to a remote server that it has been activated.
46. The method according to clause 44, wherein a controller includes re-try logic and if an initial connection is not successful, the device automatically retries to secure such connections.
47. The method according to clause 46, wherein the re-try logic can be set to re-try at particular time intervals.
48. The method according to clause 47 wherein the time interval is every 15 minutes.
49. The method according to clause 39, wherein the device is programmed to activate at least once every 24 hours to perform a dosage inventory on a blister card associated with the device.
50. The method according to any one of clauses 39-49, wherein a medication protocol requires a user to dispense one medicament from the blister card daily.
51. The method according to any one of clauses 39-49, wherein the medication protocol requires a user to dispense multiple doses daily at different administration times.

IV. Example

The following example is provided to illustrate certain features of disclosed aspects of the present disclosure. A person of ordinary skill in the art will appreciate that the scope of the disclosure is not limited to such features.

Example 1

This example concerns using disclosed aspects of a dose tracking device to produce a near real-time monitoring system for orally administered medicaments, such as anticancer drugs. Patient compliance with a medicament administration protocol is important, and the protocol depends on the medicament. Oral anticancer drugs, for example, are included in standard therapies for each cancer type. Certain anticancer drugs include a drug holiday period, whereas others must be taken on an empty stomach.

A near real-time medication monitoring system has been developed for the Cancer Research Ariake Hospital and a browser-based web portal. This system encloses an anticancer drug in a medicine pack with a communication terminal. A No. 0 capsule was sealed in a medicament pack and removal of the medicament was transmitted to the server in near real-time when the medicament was removed. The time the drug was taken out and the time it was received by the server were investigated. When the medicament was removed at Cancer Research Ariake Hospital, the event was reported to a secure browser-based web portal, via a remote server, as soon as 2 minutes after the event, such as within 2 to 20 minutes.

More particularly, confidential patient trials of a dose tracking device have been conducted. In one such trial, blister cards were inserted into 10 different dose tracking devices. The devices transmitted to a remote server the date and time when each blister card was inserted into the device. Medicament doses were then removed from the blister card by subjects according to an established protocol, and this information was transmitted to the remote server. Representative data for one such trial involving 10 patients is presented below by Table 1. The collected data included, inter alia, which pill was removed from a blister card (e.g., row 3, pill 2, highlighted in row 1 of Table 1) and at what time (e.g. 9 am).

TABLE 1

| Dose Tracking Device ID | Patient ID | Time and Blister Location of Pill Removal | | | |
|---|---|---|---|---|---|
| 1 | 986988 | A01 | R3-2:9:00 | R4-2:9:33 | R1-3:10:00 | R2-3:10:30 |
| 2 | 977771 | A02 | R3-2:9:00 | R4-2:9:33 | R1-3:10:00 | R2-3:10:30 |
| 3 | 986970 | A03 | R3-2:9:00 | R4-2:9:33 | R1-3:10:00 | R2-3:10:30 |
| 4 | 986996 | A04 | R1-3:9:00 | R3-2:9:33 | R4-2:10:00 | R2-3:10:30 |
| 5 | 978563 | A05 | R3-2:9:00 | R4-2:9:33 | R1-3:10:00 | R2-3:10:30 |
| 6 | 984348 | A06 | R1-2:9:00 | R2-2:9:33 | R3-2:10:00 | R4-2:10:30 |
| 7 | 987010 | A07 | R1-2:9:00 | R2-2:9:33 | R3-2:10:00 | R4-2:10:30 |
| 8 | 987085 | A08 | R1-2:9:00 | R2-2:9:33 | R3-2:10:00 | R4-2:10:30 |
| 9 | 986269 | A09 | R1-2:9:00 | R2-2:9:33 | R3-2:10:00 | R4-2:10:30 |
| 10 | 984827 | A10 | R1-2:9:00 | R2-2:9:33 | R3-2:10:00 | R4-2:10:30 |

This example demonstrated that the disclosed dose tracking device can be used to evaluate medication adherence in near real-time. Similar tests were conducted each day for a week. Evaluators stated that disclosed aspects of the present device "worked perfectly" during these trials.

In view of the many possible aspects to which the principles of the disclosure may be applied, it should be recognized that the disclosed aspects are only examples and do not limit the scope of the invention. Rather, the scope of the invention is defined by the following claims. I therefore claim as the invention all that comes within the scope and spirit of these claims.

I claim:

1. A dose tracking device configured for use in association with a medicament blister card, the dose tracking device comprising:
   an electronic tracking module comprising plural voltage sensors configured to be electrically coupled to a circuit trace applied to a medicament blister card such that circuits of the circuit trace align with medicament blisters containing a medicament dose; and
   one or more of a microcontroller, a rechargeable power source, a USB port, and an LED to indicate on:off and/or charging status.

2. The dose tracking device according to claim 1, wherein, when a medicament dose is dispensed from a medicament blister of the medicament blister card, a corresponding circuit of the circuit trace is broken, reducing total circuit voltage and increasing total circuit resistance, and thereby indicating that the medicament dose has been dispensed.

3. The dose tracking device according to claim 1, further comprising:
   (i) a medicament blister card receiving slot sized to pressure fit the medicament blister card with the dose tracking device; or
   (ii) shoulders that engage an inserted medicament blister card to produce a slight pucker in the inserted medicament blister card so that the medicament blister card engages the dose tracking device under tension to further secure the medicament blister card to the dose tracking device; or
   (iii) a shelf upon which at least a portion of an inserted medicament blister card is in contact to further prevent movement of the inserted medicament blister card relative to the dose tracking device; or
   (iv) alignment protrusions to facilitate aligning the dose tracking device with the medicament blister card and the circuit trace; or
   (v) any combination of two or more of (i), (ii), (iii), and (iv).

4. The dose tracking device according to claim 1, further comprising plural metal clamps configured to firmly associate the dose tracking device with the medicament blister card.

5. The dose tracking device according to claim 4, further comprising J clamps configured to engage clamp protrusions to lock the plural metal clamps in place.

6. The dose tracking device according to claim 1, further comprising a control board for controlling device functions.

7. The dose tracking device according to claim 6, further comprising plural electrical connectors for electrical connection with the circuit trace.

8. The dose tracking device according to claim 1, the dose tracking device comprising an electronic tracking module that comprises:
   a medicament blister card receiving slot sized to provide a pressure fit for a medicament blister card inserted into the dose tracking device, the dose tracking device further comprising shoulders configured to engage an inserted medicament blister card to produce a slight pucker in the inserted medicament blister card so that the medicament blister card engages the dose tracking device under tension and a shelf upon which at least a portion of the medicament blister card is in contact to further prevent movement of the medicament blister card relative to the dose tracking device;
   plural voltage sensors configured to electrically couple to a circuit trace applied to the medicament blister card when the medicament blister card and circuit trace are inserted into the dose tracking device, the circuit trace comprising plural conductive metal pads configured to provide electrical connection to the dose tracking device, and plural semiconductor circuit traces that align with medicament blisters on the medicament blister card, such that when a medicament dose is expelled from a medicament blister, a corresponding circuit of the circuit trace is broken, thereby reducing total circuit voltage and increasing total circuit resistance, indicating that the medicament dose has been dispensed;

alignment protrusions to facilitate aligning the dose tracking device with the medicament blister card and the circuit trace;

plural metal clamps to hold the medicament blister card in position relative to the dose tracking device; and a control board for controlling dose tracking device functions.

9. The dose tracking device according to claim 8, further comprising J-clamps that are configured to deflect upon insertion of a medicament blister card and return to an undeflected position to secure the dose tracking device to the medicament blister card.

10. The dose tracking device according to claim 1, wherein the dose tracking device is a unitary device, a clam shell device, or a device comprising separable components.

11. The dose tracking device according to claim 1, wherein the dose tracking device is configured for use with a 4-inch×8-inch medicament blister card.

12. The dose tracking device according to claim 1, further in association with a remote server for receiving data from the dose tracking device.

13. The dose tracking device according to claim 1, further comprising re-try logic whereby the dose tracking device periodically attempts to connect with the medicament blister card and/or attempts to transmit data to the remote server.

14. The dose tracking device according to claim 1, wherein the dose tracking device is a cellular connected device, a short-range wireless device, a WiFi device, or any combination thereof.

15. An adhesive circuit trace configured for electrical connection with a device according to claim 1, the adhesive circuit trace comprising:

a front side comprising
plural metal conductive pads for electrical association with a dose tracking device,
plural circuits electrically associated with the metal conductive pads wherein the plural circuits are configured to align with medicament blisters on a medicament blister card and to measure voltage or resistance across an individual circuit aligned with each medicament blister, and
plural connector traces for interconnecting the dose tracking device to the plural circuits, wherein each of the plural connector traces is connected to at least one of the plural conductive metal pads, and wherein the plural connector traces are configured in pairs with each pair connected in parallel to opposing ends of each of two or more of the plural circuits; and a back side comprising an adhesive for securing the adhesive circuit trace to the medicament blister card.

16. A combination, comprising:
a dose tracking device according to claim 1; and
a medicament blister card comprising an adhesive circuit trace that is applied to the medicament blister card and electrically associated with the dose tracking device, the adhesive circuit trace comprising a front side comprising
plural metal conductive pads for electrical association with a dose tracking device,
plural circuits electrically associated with the metal conductive pads wherein the plural circuits are configured to align with medicament blisters on a medicament blister card and to measure voltage or resistance across an individual circuit aligned with each medicament blister, and
plural connector traces for interconnecting the dose tracking device to the plural circuits, wherein each of the plural connector traces is connected to at least one of the plural conductive metal pads, and wherein the plural connector traces are configured in pairs with each pair connected in parallel to opposing ends of each of two or more of the plural circuits; and a back side comprising an adhesive for securing the adhesive circuit trace to the medicament blister card.

17. A method for dispensing a medicament dose, comprising using a dose tracking device according to claim 1, or a combination comprising the dose tracking device and a medicament blister card comprising an adhesive circuit trace that is applied to the medicament blister card and electrically associated with the dose tracking device, the adhesive circuit trace comprising a front side comprising
plural metal conductive pads for electrical association with a dose tracking device,
plural circuits electrically associated with the metal conductive pads wherein the plural circuits are configured to align with medicament blisters on a medicament blister card and to measure voltage or resistance across an individual circuit aligned with each medicament blister, and
plural connector traces for interconnecting the dose tracking device to the plural circuits, wherein each of the plural connector traces is connected to at least one of the plural conductive metal pads, and wherein the plural connector traces are configured in pairs with each pair connected in parallel to opposing ends of each of two or more of the plural circuits; and a back side comprising an adhesive for securing the adhesive circuit trace to the medicament blister card.

18. The method according to claim 17, further comprising providing the dose tracking device to a user.

19. The method according to claim 18, further comprising instructing the user to insert the medicament blister card into the dose tracking device to appropriately align the adhesive circuit trace with electrical sensors on the dose tracking device.

20. The method according to claim 17, wherein the dose tracking device is activated upon insertion of a medicament blister card and the dose tracking device attempts an initial measurement.

21. The method according to claim 20, wherein:
the dose tracking device is appropriately connected to the medicament blister card and the dose tracking device transmits to a remote server that it has been activated; or
a controller includes re-try logic and if an initial connection is not successful, the dose tracking device automatically retries to secure an initial connection.

22. The method according to claim 17, wherein the dose tracking device is programmed to activate at least once every 24 hours to perform a dosage inventory on a medicament blister card associated with the dose tracking device.

* * * * *